US00PP30908P2

(12) United States Plant Patent
Stemkens

(10) Patent No.: US PP30,908 P2
(45) Date of Patent: Sep. 24, 2019

(54) ***COREOPSIS* PLANT NAMED 'CSGZ0005'**

(50) Latin Name: *Coreopsis grandiflora*
Varietal Denomination: CSGZ0005

(71) Applicant: SYNGENTA PARTICIPATIONS AG, Basel (CH)

(72) Inventor: Henricus Godefridus Wilhelmus Stemkens, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/999,993

(22) Filed: Sep. 7, 2018

(51) Int. Cl.
*A01H 5/02* (2018.01)
*A01H 6/14* (2018.01)

(52) U.S. Cl.
USPC ..... Plt./417

(58) Field of Classification Search
USPC ..... Plt./263.1, 417
See application file for complete search history.

*Primary Examiner* — Susan McCormick Ewoldt
*Assistant Examiner* — Karen M Redden
(74) *Attorney, Agent, or Firm* — Dale Skalla

(57) ABSTRACT

A new and distinct *Coreopsis* plant named 'CSGZ0005' particularly distinguished by a compact plant habit and dense branching. Flowers are double and bright yellow colored.

1 Drawing Sheet

Latin name of the genus and species of the plant claimed: *Coreopsis grandiflora.*

Varietal denomination: 'CSGZ0005'.

BACKGROUND OF THE INVENTION

The new *Coreopsis* cultivar is a product of a planned breeding program conducted by the inventor in Enkhuizen, The Netherlands. The objective of the breeding program was to produce new *Coreopsis* varieties. The open pollination resulting in this new variety was made during August of 2013.

The seed parent is the unpatented, propriety variety referred to as 'Q5310-1'. The pollen parent is 'Q5309-1', not patented. The new variety was discovered in July of 2014 by the inventor in a group of seedlings resulting from the 2012 crossing in a greenhouse in Enkhuizen, The Netherlands.

Asexual reproduction of the new cultivar 'CSGZ0005' was first performed by terminal vegetative cuttings during September of 2014 at a greenhouse in Enkhuizen, The Netherlands. Subsequent propagation by vegetative cuttings has shown that the unique features of this cultivar are stable and reproduced true to type in more than 20 successive generations.

BRIEF SUMMARY OF THE INVENTION

The cultivar 'CSGZ0005' has not been observed under all possible environmental conditions. The phenotype may vary somewhat with variations in environment such as temperature, day length, and light intensity, without, however, any variance in genotype.

A Plant Breeder's Right for this cultivar was applied for in the European Union on Aug. 2, 2018 and assigned No. 2018/2014. 'CSGZ0005' has not been made publicly available prior to the effective filing date of this application, notwithstanding any disclosure that may have been made less than one year prior to the effective filing date of this application by the inventor or another who obtained 'CSGZ0005' directly from the inventor.

The following traits have been repeatedly observed and are determined to be the unique characteristics of 'CSGZ0005'. These characteristics in combination distinguish 'CSGZ0005' as a new and distinct *Coreopsis* cultivar: 1. Distinctive bright yellow double flower color 2. Compact plant habit. 3. Very uniform radial plant shape. 4. Full, dense plant.

PARENT COMPARISON

Plants of the new cultivar 'CSGZ0005' are similar to plants of the female seed parent, most horticultural characteristics, however, plants of the new cultivar 'CSGZ0005' differ in the following; 1. Plant habit of the new variety is compact and round. The female seed parent is an upright plant. 2. New variety is shorter than the female seed parent. 3. Shorter peduncles than the female seed parent.

Plants of the new cultivar 'CSGZ0005' are similar to plants of the male seed parent, most horticultural characteristics, however, plants of the new cultivar 'CSGZ0005' differ in the following: 1. Plant habit of the new variety is compact and round. The male seed parent is an upright plant. 2. New variety is shorter than the male seed parent. 3. Flowers of the new variety are smaller than those of the male seed parent.

TABLE 1

DIFFERENCES BETWEEN THE NEW VARIETY AND A MOST SIMILAR VARIETY

| | 'CSGZ0005' | 'DECORE016' (U.S. Plant Pat. No. 25,241) |
|---|---|---|
| Flower size: | Smaller | Larger |
| Foliage color: | Darker | Lighter |
| Flowers: | Flowers less double | Flowers more double |

BRIEF DESCRIPTION OF THE PHOTOGRAPHS

Figure 1:
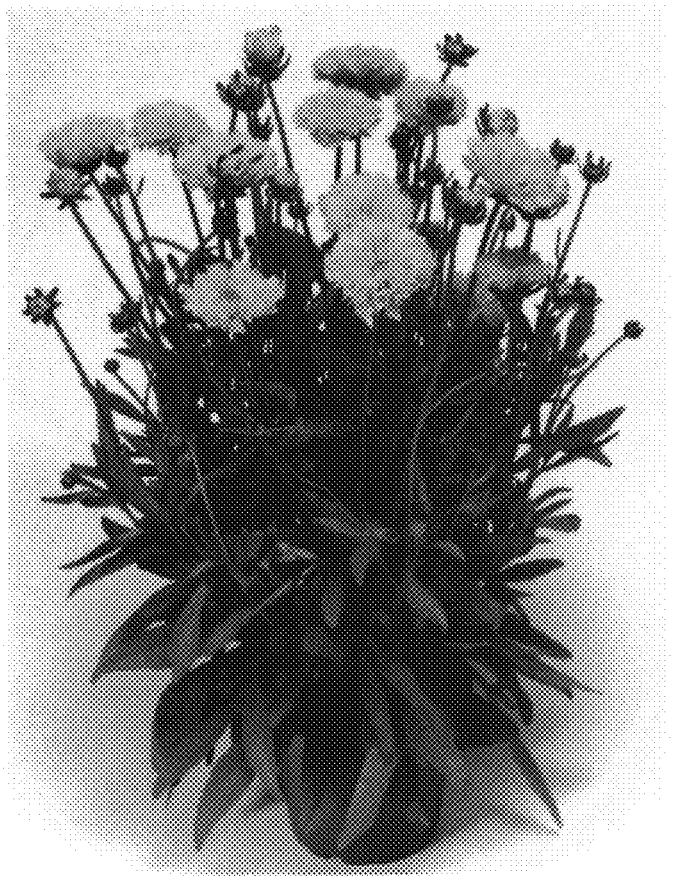
FIG. 1 illustrates in full color a typical plant of 'CSGZ0005' grown in 13 cm pots outdoors in Enkhuizen, The Netherlands.
Figure 2:
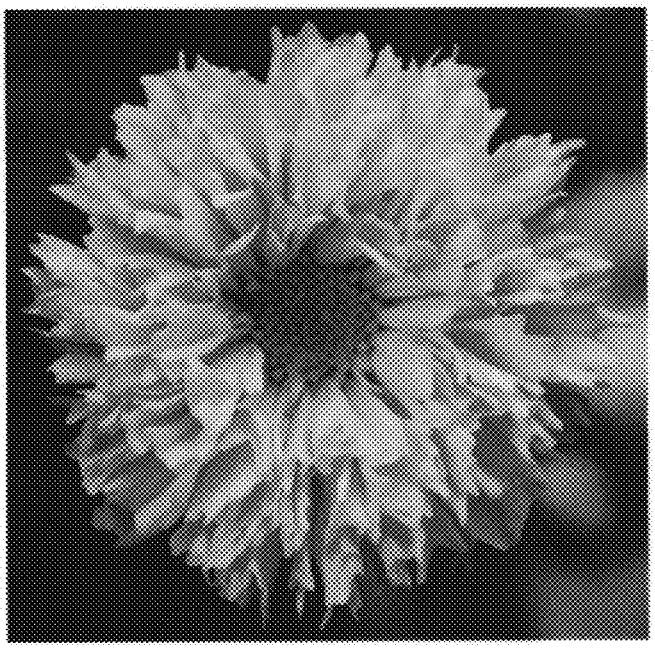
FIG. 2 illustrates in full color multiple typical inflorescence of 'CSGZ0005'. Age of the plant photographed is approximately 10 weeks from a rooted cutting in a 13 cm pot.

The photographs were taken using conventional techniques and although colors may appear different from actual colors due to light reflectance it is as accurate as possible by conventional photographic techniques.

DETAILED BOTANICAL DESCRIPTION

The following observations and measurements describe 'CSGZ0005' plants grown in a greenhouse in Enkhuizen, The Netherlands under natural lighting. Measurements were taken during April of 2016. The plants were approximately 10 weeks old from a rooted cutting in a 13 cm pot. Measurements and numerical values represent averages of typical plant types.

Color references are made to The Royal Horticultural Society Colour Chart (R.H.S.) 2001.

Propagation:

*Time to initiate rooting.*—

*Summer.*—3 to 4 days at approximately 25 degrees C.

*Winter.*—4 to 5 days at approximately 25 degrees C.

*Total rooting time.*—About 14 days at approximately 25 degrees C. for a fully rooted cutting.

*Root description.*—Well branched, fleshy and white, color RHS 155B.

Plant:

*Growth habit.*—Mounded.

*Height.*—Approximately 30 to 35 cm.

*Plant spread.*—Approximately 25 cm.

*Growth rate.*—Moderate.

*Branching characteristics.*—Well branched, basal branching.

*Length of lateral branches.*—Approximately 13 cm.

*Diameter of lateral branches.*—Approximately 0.4 cm.

*Texture of lateral branches.*—Glossy with very light and delicate hair, slightly ribbed longwise.

*Internodes length.*—Approximately 4 cm.

*Strength of stem.*—Flexible and strong, not likely to break.

*Color of lateral branches.*—RHS 144A.

*Aspect/angle of branches.*—Straight, occurring at approximately 45 degree from ground level.

*Number of leaves per lateral branch.*—Approximately 17.

Foliage:

*Leaf.*—

*Arrangement.*—Sub opposite or whorled from base.

*Average length.*—Approximately 6 to 7 cm.

*Average width.*—Approximately 3.5 cm.

*Shape of blade.*—Oblanceolate.

*Apex.*—Acute.

*Base.*—Acuminate.

*Attachment.*—Petiolate.

*Margin.*—Entire.

*Texture of top surface.*—Very light and delicate hair.

*Texture of bottom surface.*—Very light and delicate hair.

*Color.*—

*Young foliage upper side.*—RHS 137A.

*Young foliage under side.*—RHS 147B.

*Mature foliage upper side.*—RHS 137B.

*Mature foliage under side.*—RHS 148B.

*Venation.*—

*Type.*—Reticulate.

*Venation color upper side.*—RHS N137A.

*Venation color under side.*—RHS N137B.

*Petiole.*—

*Length.*—2.6 cm.

*Diameter.*—0.3 cm.

*Pubescence.*—Very light and delicate hair.

*Color.*—RHS 144A.

Flower:

*Bloom period.*—In moderate climate zones, USDA Zone 7 and up blooming occurs from Spring to late Fall; In cooler climate zones from Summer until Fall.

Bud:

*Bud shape.*—Oblate.

*Bud length.*—Approximately 0.6 cm.

*Bud diameter.*—Approximately 1.1 cm.

*Bud color.*—The bud is bi-color forming alternate stripes RHS 147A and RHS 153B.

Inflorescence:

*Form.*—Composite, double occurring.

*Lastingness.*—Individual flowers last approximately 7 to 12 days, depending on environmental conditions.

*Flower.*—

*Diameter of entire flower.*—Approximately 5 cm.

*Depth of flower.*—Approximately 1.5 cm.

*Diameter of disc.*—Approximately 1.5 cm.

*Depth of disc.*—Approximately 0.7 cm.

Ray florets:

*Number of ray florets.*—32.

*Average length.*—Approximately 2.2 cm.

*Width.*—Approximately 1.8 cm.

*Apex shape.*—Praemorse.

*Margin.*—Entire.

*Color.*—

*Upper surface at first opening.*—RHS 4A.

*Upper surface at maturity.*—RHS 4B.

*Upper surface at fading.*—RHS 4C.

*Under surface at first opening.*—RHS 3A.

*Under surface at maturity.*—RHS 4A.

*Under surface at fading.*—RHS 4B.

Disc florets:

*Number of disc florets.*—Approximately 100.

*Length.*—Approximately 0.7 cm.

*Width.*—Approximately 0.2 cm.

*Shape.*—Tubular with 5 lobes on tip.

*Margin.*—Entire.

*Color.*—

*At first opening.*—RHS 17B.

*At maturity.*—RHS 15A.

*At fading.*—RHS 22B.

*Fragrance.*—Very delicate, sweet scent.

*Outer/involucral bracts.*—

*Number.*—Approximately 12.

*Sepal length.*—Approximately 1.2 cm.

*Sepal width.*—Approximately 0.4 cm.

*Sepal texture.*—Ribbed longwise, stiff and glossy (like plastic).

*Apex shape.*—Acute.

*Margin.*—Entire.

*Color.*—RHS 137B.

Peduncle:

*Peduncle length.*—Approximately 10 cm.

*Peduncle diameter.*—Approximately 0.2 cm.

*Angle.*—Approximately 90 degree from center of whorl.

*Color.*—RHS 144A.

*Strength.*—Flexible.

*Peduncle texture.*—Glabrous, shiny and slightly ribbed longwise.

Reproductive organs:

Disc florets:

*Androecium.*—Present Androecium of 5 stamens, these fused by their anthers, surrounding the style.

*Stamens.*—Present, quantity of 5 per floret.

*Anther shape.*—Linear and flat.

*Anther length.*—Approximately 0.25 cm.

*Anther color.*—RHS 186A.

*Pollen quantity.*—Moderate.

*Gynoecium.*—Present, ovary inferior, gynoecium of two fused carpels.

*Pistil number.*—1 per floret.

*Pistil shape.*—Cylindrical oblong tube with two branched at tip.

*Pistil length.*—Approximately 0.65 cm.

*Style length.*—Approximately 0.3 cm.

*Style color.*—RHS 145D.

*Stigma shape.*—V shaped with two, curved downward, branched-at tip.

*Stigma color.*—RHS N25C.

*Ovary Length.*—0.2 cm.

*Ovary color.*—RHS 149A.

*Ray florets.*—No reproductive structures present.

Other characteristics:

Seeds and fruits: Has not been observed.

Disease/pest resistance: Typical to known *Coreopsis* varieties. Neither resistance nor susceptibility to the normal diseases and pests of *Coreopsis* have been observed. Pests common to *Coreopsis* include Aphids and thrips. Typical diseases are Botrytis and Pythium.

Temperature tolerance: To USDA Zone 5. Other tolerance: Tolerant to hot, humid Summer climates.

What is claimed is:

1. A new and distinct cultivar of *Coreopsis* plant named 'CSGZ0005', as substantially illustrated and described herein.

* * * * *